(12) United States Patent
Faour

(10) Patent No.: US 6,753,011 B2
(45) Date of Patent: *Jun. 22, 2004

(54) COMBINED DIFFUSION/OSMOTIC PUMPING DRUG DELIVERY SYSTEM

(75) Inventor: Joaquina Faour, Buenos Aires (AR)

(73) Assignee: Osmotica Corp, Tortola (VG)

( * ) Notice: Subject to any disclaimer, the term of this patent is extended or adjusted under 35 U.S.C. 154(b) by 98 days.

This patent is subject to a terminal disclaimer.

(21) Appl. No.: 10/047,915

(22) Filed: Jan. 15, 2002

(65) Prior Publication Data

US 2002/0132005 A1 Sep. 19, 2002

Related U.S. Application Data

(63) Continuation-in-part of application No. 09/483,282, filed on Jan. 14, 2000, now Pat. No. 6,352,721.

(51) Int. Cl.⁷ .............................. A61K 9/22; A61K 9/24; A61K 9/32; A61K 9/36; A61K 9/44
(52) U.S. Cl. ...................... 424/473; 424/468; 424/472; 424/480; 424/482; 514/772.3; 514/781; 514/783; 514/784; 514/785; 514/786
(58) Field of Search .................... 424/464, 465, 424/468, 471, 472, 474, 475, 479, 480, 467, 482

(56) References Cited

U.S. PATENT DOCUMENTS

| | | |
|---|---|---|
| 4,235,236 A | 11/1980 | Theeuwes |
| 4,693,886 A | 9/1987 | Ayer |
| 4,765,989 A | 8/1988 | Wong et al. |
| 4,859,470 A | 8/1989 | Guittard et al. |
| 4,968,507 A | 11/1990 | Zentner et al. |
| 5,516,527 A | 5/1996 | Curatolo |
| 5,543,155 A | 8/1996 | Fekete et al. |
| 6,352,721 B1 * | 3/2002 | Faour .......................... 424/473 |

FOREIGN PATENT DOCUMENTS

| | | |
|---|---|---|
| EP | 1027888 A2 | 8/2000 |
| GB | 2074860 B | 2/1984 |

* cited by examiner

Primary Examiner—James M. Spear
(74) Attorney, Agent, or Firm—Rick Matos; Innovar, L.L.C.

(57) ABSTRACT

Delivery devices capable of delivering one or more active substances by diffusion through plural micropores in the membrane (4) or by osmotic pumping through one or more preformed passageways (5) in the membrane are provided. The device (1) has an about centrally located expandable core (2) completely surrounded by an active substance-containing layer (3), which is completely surrounded by the membrane. The device is capable of delivering insoluble, slightly soluble, sparingly soluble and very soluble active substances to an environment of use. The preferred delivery rate is zero order. The device can deliver an active substance for a period of about 12–24 hours.

30 Claims, 4 Drawing Sheets

COMBINED DIFFUSION/OSMOTIC PUMPING DRUG DELIVERY SYSTEM

CROSS-REFERENCE TO EARLIER FILED APPLICATIONS

The present application is a continuation-in-part of application Ser. No. 09/483,282 filed Jan. 14, 2000 now U.S Pat. No. 6,352,721.

FIELD OF THE INVENTION

This invention pertains to a delivery device for the controlled release of active agents to an environment of use. More particularly, the invention pertains to a device for the delivery of active agents over a prolonged and extended period of time. The controlled delivery device comprises an expandable-hydrophilic polymer-core located substantially in the center of the dosage form surrounded by a composition of the active agent(s) to be delivered. A novel dual function membrane permits delivery of the active agent(s) through a combination of diffusion and osmotic pumping mechanisms.

BACKGROUND OF THE INVENTION

Osmotic devices have demonstrated utility in delivering beneficial active agents, such as medicines, nutrients, food, pesticides, herbicides, germicides, algaecides, chemical reagents, and others, to an environment of use in a controlled manner over prolonged periods of time. Known devices include tablets, pills, and capsules.

Several advancements have been made in the art to improve the delivery of insoluble or slightly soluble products to an environment of use. The prior art has focused on the development of new membranes that deliver active agents by diffusion and/or osmotic pumping.

U.S. Pat. No. 4,235,236 to Theeuwes discloses an osmotic device that delivers drug by the combined mechanisms of diffusion and osmotic pumping. The device comprises a microporous wall surrounding a compartment containing an active agent and an expandable member. The expandable member consists of a semipermeable, flexible or expandable film surrounding a member selected from the group consisting of an osmotically effective solute, a gas generating couple and a swellable polymer. The external wall of the device is formed of a microporous material through which the active agent is delivered. This patent does not disclose the inclusion of a passageway in the external wall to provide delivery by osmotic pumping and diffusion. Even though the solution proposed by U.S. Pat. No. 4,235,236 allows the release of an active agent at a steady rate—the so called zero-order release—, it requires the manufacturing of an elastic film that separates the expandable member from the composition comprising the active agent. The adhesion process between said membrane and said composition comprising the active agent requires complicated processing steps that make the formulation very expensive.

U.S. Pat. No. 4,327,725 to Cortese and Theeuwes, discloses an osmotic device comprising a semipermeable wall surrounding two layers, one layer containing an active agent and the other an expandable hydrogel. A passageway in the wall communicates the active agent layer with the environment of use. The patent describes the use of cellulose acylate as the material comprising the semipermeable membrane.

U.S. Pat. Nos. 5,612,059 and 5,698,220 to Cardinal et al., disclose the use of asymmetric membranes in delivery devices. These membranes may be permeable, semipermeable, perforated or unperforated and can deliver an active substance by the combined mechanisms of diffusion and osmotic pumping. These patents also disclose the formation of asymmetric membranes with 398-10 (Eastman) cellulose acetate.

EP 636366 and EP 553392 disclose an active agent composition coated with an aqueous dispersion of plasticized acrylic polymer, which is subjected to a particular curing process. The controlled release formulation disclosed in these applications has a stable dissolution profile despite exposure to a variety of storage conditions.

U.S. Pat. No. 5,543,155 to Fekete et al. discloses a controlled delivery pharmaceutical composition core surrounded by a wall comprising an ammonium methacrylate copolymer that is permeable to low molecular weight (MW) molecules. This controlled delivery pharmaceutical composition contains an active pharmaceutical compound and hydroxypropyl methylcellulose (HPMC) as the hydrophilic polymer. Low MW osmagents are not incorporated into the composition. Tablets having a bi-layered core are prepared with a hydrophilic polymer layer comprising high molecular weight HPMC, which has a viscosity higher than 1000 cP in a 2% aqueous solution.

U.S. Pat. No. 5,543,155 also discloses various combinations of Eudragit™ RL (easily permeable films) and Eudragit™ RS (not easily permeable films). The use of a permeable membrane alone, however, does not allow the inclusion of a low molecular weight osmotic agent in the pharmaceutical composition tablet core (for example, potassium chloride, sodium tartrate, sodium chloride, sodium sulfate, etc.). Thus, it limits the versatility of the device to the delivery of active agents that require a significant absorption of liquid to achieve an effective and constant delivery of solution or suspension of the active agent from the device. Osmotic devices having a bi-layered core, one layer containing the active agent and the other being a swellable placebo layer, surrounded by a semipermeable membrane possess significant disadvantages. The placebo layer consists mainly of a swellable polymer and/or a hydrogel that, while absorbing fluid from the environment of use, expands and exerts pressure over the layer that contains the active agent thereby releasing the active agent through a passageway in the wall. The prior art teaches that perforation of the semipermeable membrane needs to be carried out selectively on the side of the membrane that is adjacent to the layer comprising the active agent. In fact, if the membrane is perforated adjacent the placebo layer, the active agent will not be released. If two perforations are carried out, one adjacent the active-agent layer and the other adjacent the swellable polymer layer ("push" layer), both the active agent and the swellable polymer are released, resulting in loss of the "push" effect. The device would therefore act as a simple osmotic pump that would not allow the release of the entire charge of active agent in the dosage form. The precise selection of which portion of the membrane should be drilled requires the use of color or shape coding in order to distinguish the layers, as well as meticulous handling of the devices. The handling of the devices requires the use of sophisticated and expensive electronic equipment able to recognize the different layers of the tablet core.

U.S. Pat. No. 5,543,155 also discloses perforation of the membrane adjacent both layers of the core; however, a specific high molecular weight polymer (HPMC) is required to prevent the loss of the push layer leaving a significant number of available hydrophilic polymers unavailable for use in these devices.

U.S. Pat. No. 5,516,527 to Curatolo discloses a device that can include a preformed passageway and plural pores.

The device requires the formation of a phase-separated coating that ultimately forms a porous membrane.

While the prior art discloses a wide variety of osmotic devices, no single device has been found to be generally applicable and, in fact, most known devices are designed to operate within a relatively narrow range of conditions. For example, a first formulation of an osmotic device may be generally useful for delivering slightly to sparingly water soluble components to an environment of use, but that same formulation will require drastic changes in order to deliver a very water soluble component and vice versa. In addition, diffusion controlled devices are generally useful for delivering sparingly to very, but not slightly, water soluble components to an environment of use. Therefore, a need remains for a delivery device capable of delivering components having very different solubilities to an environment of use without requiring a dramatic reformulation of the device.

SUMMARY OF THE INVENTION

The present invention provides a controlled release device for active substances comprising an external dual delivery membrane having at least one preformed passageway and plural micropores, wherein the device releases the active agent through a combination of diffusion and osmotic pumping. The at least one passageway can be located anywhere in the dual delivery membrane.

The present invention also provides a controlled release device having an approximately centrally located core comprising a hydrophilic expandable polymer and, optionally, an osmagent, wherein the core is surrounded by a composition comprising at least one active agent and preferably an osmagent and/or an osmopolymer. During operation in an environment of use, the hydrophilic core imbibes fluid and increases in volume thereby forcing release of the active agent(s) through either the pores of the membrane by diffusion and/or the passageway by osmotic pumping effect.

The invention also provides a therapeutic device for the delivery of pharmaceutically active agents, ranging in solubility from slightly soluble to very soluble drugs, in a controlled, continuous and approximately steady, preferably zero order, rate over a prolonged period of time.

The invention also provides a smaller than usual dosage form that delivers active compounds by diffusion through the entire surface of the device. In this way, a portion of the membrane that releases active compounds is doubled with respect to conventional bi-layered devices.

The invention also provides a controlled release device containing a high or low molecular weight osmagent inside the core of the device, thereby enabling the device to absorb greater quantities of fluid, deliver a greater range of active agents irrespective of their solubility, and deliver the active agents by diffusion and/or osmotic pumping.

The device of the present invention may optionally be provided with an external coating comprising one or more active agents for immediate delivery to the environment of use.

Accordingly, one aspect of the present invention provides an improved device for the controlled delivery of active agents to an environment of use, wherein the device comprises:

a) a core located approximately at the center of the device and comprising at least one expandable hydrophilic polymer and optionally an osmagent, the core being able to absorb and/or imbibe fluids from one environment of use;

b) a composition immediately surrounding the core comprising at least one active substance and, optionally, an osmagent and/or an osmopolymer;

c) a membrane immediately surrounding the composition and comprising a mixture of a cellulose acylate (ester), a methacrylate salt copolymer and a plasticizer, wherein the membrane permits delivery of the at least one active substance through a combination of diffusion and osmotic pumping; and d) at least one preformed passageway and plural micropores in the membrane that communicate the composition with the outside of the device.

Another aspect of the invention provides a device for the controlled delivery of at least one active agent to an environment of use, wherein the device comprises:

a core expandable in a fluid from the environment of use, the core being approximately centrally located in the device;

a layer comprising at least one first active agent, wherein the layer is in contact with and surrounds the core; and a membrane in contact with and surrounding the layer and comprising at least one preformed passageway for delivery of the at least one active agent by osmotic pumping and plural micropores for delivery of the at least one active agent by diffusion, and the membrane further comprising one or more cellulose esters, one or more poly(methacrylate) copolymer salts and one or more plasticizers, wherein the membrane permits delivery of the at least one active substance through a combination of diffusion and osmotic pumping.

Specific embodiments of the invention include those wherein: 1) the device further comprises a drug-containing coat external to the membrane, wherein the drug-containing coat comprises a second active agent, provides an immediate, rapid, controlled and/or delayed release of the second active agent and the external coat surrounds at least a portion of the membrane; 2) the first and second active agents are different and are independently selected at each occurrence from the group consisting of an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, antidepressant agent, antidiabetic agent, antineoplastic agent, anti-psychotic agent, neuroleptic agent, antihypertensive agent, hypnotic agent, sedative agent, anxiolytic energizer agent, antiparkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, anti-ulcerant agent, anti-flatulent agent, anti-incontinence agent, and cardiovascular agent; 3) the first active agent is a prokinetic agent and the second active agent is a gastric acid secretion inhibitor agent; 4) the first active agent is a decongestant and the second active agent is an antihistamine; 5) the first active agent is a first anti-incontinence agent and the second active agent is a different second anti-incontinence agent; 6) the anti-incontinence agents are selected from the group consisting of oxybutynin, tolterodine and darifenacin; 7) the first active agent is a first antihypertensive agent and the second active agent is a different second antihypertensive agent; 8) the antihypertensive agents are selected from the group consisting of a calcium channel blocker agent, an angiotensin converting enzyme inhibitor agent, a diuretic agent and a beta-adrenergic antagonist agent; 9) the first active agent is an antidepressant agent and the second active agent is an anti-psychotic agent; 10) the first active agent is a first analgesic or, anti-inflammatory agent and the second active agent is a different second analgesic or, anti-inflammatory agent; 11) the analgesic and anti-inflammatory agents are selected from the group consisting of an non-steroidal anti-inflammatory agent, a steroidal anti-inflammatory agent, an opioid receptor agonist agent, and a selective or specific COX-II inhibitor agent; 12) the first active agent is an antiviral agent and the second active agent is an antihistamine agent; 13) the first active agent is a muscle relaxant agent and the second active agent is an anti-inflammatory or analgesic agent; 14) the first active agent is pridinol and the second active agent is a selective or specific COX-II inhibitor agent; 15) the first and second active agents are the same; 16) the membrane comprises about 1 to 99 weight percent of one or more cellulose esters, about 84 to 0.5 weight percent of one or more poly(methacrylate) copolymer salts and about 15 to 0.5 weight percent of one or more plasticizers; 17) the cellulose ester is selected form the group consisting of cellulose acylate, cellulose diacylate, cellulose triacylate, cellulose acetate, cellulose diacetate, cellulose triacetate and combinations thereof; 18) the poly(methacrylate) copolymer salt is poly(ammonium methacrylate) copolymer; 19) the layer further comprises at least one of an osmagent and an osmopolymer; the expandable core further comprises at least one expandable hydrophilic polymer and, optionally, an osmagent; 20) the expandable hydrophilic polymer is one or more of hydroxypropyl methylcellulose, alkylcellulose, hydroxyalkylcellulose, poly(alkylene oxide), and combinations thereof; and the at least one cellulose ester is independently selected from the group consisting of cellulose acylate, cellulose diacylate, cellulose triacylate, cellulose acetate, cellulose diacetate, cellulose triacetate and combinations thereof; 21) the core excludes an active agent; 22) the membrane comprises a mixture of a cellulose acylate, a poly(methacrylate) copolymer salt and a plasticizer; 23) a slightly soluble or insoluble active substance is delivered predominantly through the at least one passageway and a soluble or sparingly soluble active substance is delivered predominantly through the plural micropores; and/or 24) the active substance is delivered at an approximately zero order rate.

Active agents can include compounds such as biologically or pharmacologically active agents, medicines, nutrients, food products, insecticides, pesticides, herbicides, germicides, algaecides, fungicides, chemical reagents, growth regulating substances, parasiticides, sex sterilants, fertility promoters, biocides, rodenticides, disinfectants, anti-oxidants, plant growth promoters, preservatives, fermentation agents, fertility inhibitors, deodorants, microorganism attenuators, catalysts, food supplements, cosmetics, vitamins, and other agents that benefit the environment of use.

Preferred embodiments of the invention include those wherein the active substance is pharmacologically or biologically active or wherein the environment of use is the GI tract of a mammal.

Other preferred embodiments of the device of the invention are used in biological environments including the oral, ocular, nasal, vaginal, glandular, gastrointestinal tract, rectal, cervical, intrauterine, arterial, venous, otic, sublingual, dermal, epidermal, subdermal, implant, buccal, bioadhesive, mucosal and other similar environments. Likewise, it may be used in aquariums, industrial warehouses, laboratory facilities, hospitals, chemical reactions and other facilities.

Other features, advantages and embodiments of the invention will become apparent to those of ordinary skill in the art by the following description, accompanying examples and appended claims.

BRIEF DESCRIPTION OF THE DRAWINGS

The following drawings are given by way of illustration only, and thus are not intended to limit the scope of the present invention. The drawings are not drawn to scale.

FIG. 1-*b* is a sectional view of the device of FIG. 1-*a*, wherein the core has been expanded by imbibing a fluid.

DETAILED DESCRIPTION OF THE INVENTION

Figure 1A:
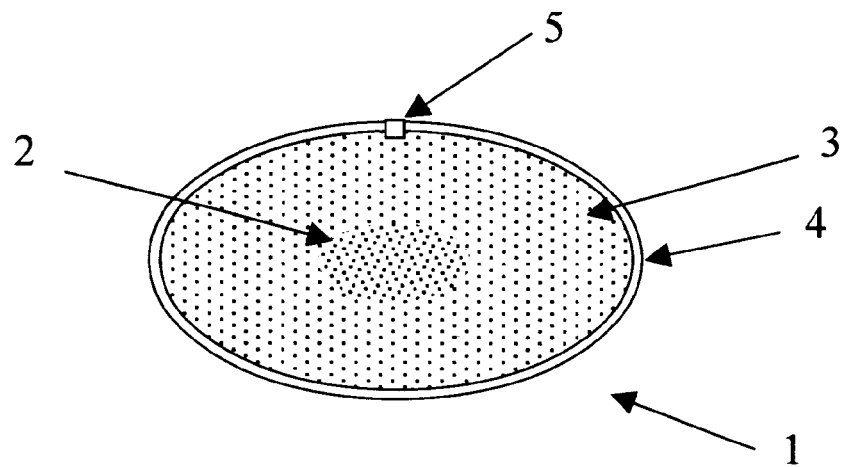
FIG. 1-*a* is a sectional view of an oral device according to the present invention.
Figure 1B:
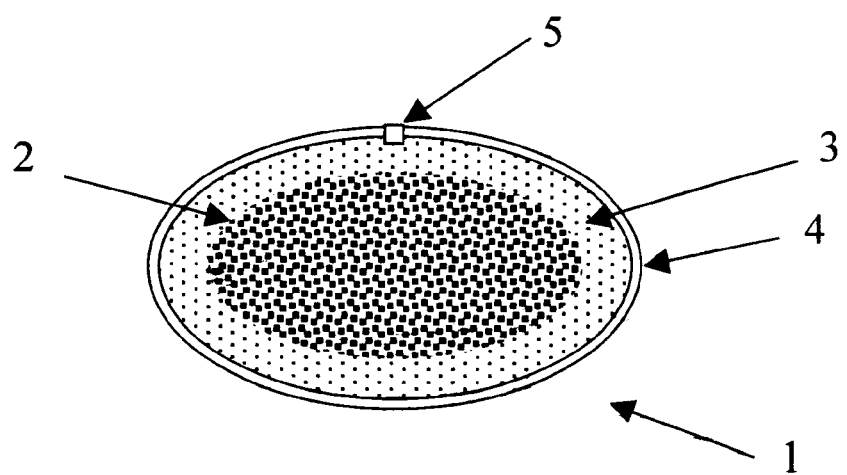

FIG. 1-*a* depicts an oral dosage form device (1) comprising an approximately centrally located core (2) comprising an expandable hydrophilic polymer composition capable of absorbing, or imbibing, fluids. The core (2) is surrounded by and in contact with a layer (3), which comprises at least one active agent and optionally an osmotically effective solute. The layer (3) is surrounded by and in contact with a wall (4) having pores (not shown) and a preformed passageway (5). The device delivers the active gent by diffusion and osmotic pumping. The wall (4) is preferably physiologically inert and preserves its physical and chemical integrity during delivery of the active agents comprised in the layer (3).

The beneficial agent(s) comprised in the layer (3) is delivered from the delivery device (1) generally as follows. Fluid is imbibed from an environment through the membrane (4) into the device (1). The fluid then permeates the layer (3). The hydrophilic core (2) imbibes the fluid and swells pushing the aqueous solution or suspension formed from the layer (3) towards the membrane (4). The beneficial agent is released from the dosage form by molecular diffusion across the membrane (4) and/or by osmotic pumping through the passageway (5) in the membrane.

FIG. 1-*b* depicts the device of FIG. 1-*a* in operation delivering the active agent in the layer (3). During operation, the hydrophilic polymer composition of the core (2) absorbs fluid that enters the device (1) across the wall (4) and swells, or expands. FIG. 1-*b* depicts the enlarged core pushing the active agent through the wall and passageway.

The layer preferably completely surrounds the expandable core, thereby promoting isotropic diffusion and thus providing an about zero order release profile.

The inclusion of an about centrally located expandable hydrophilic polymer core in the present delivery device allows delivery of the active agent by isotropic diffusion, thus providing a steady release rate, that is about zero order release profile. The isotropic diffusion process provides a release profile closer to the desired zero order release profile while anisotropic diffusion provides a release profile with an accelerated initial release.

The portion of active agent that is delivered by diffusion or osmotic pumping generally depends upon the diffusivity of the active agent through the wall (4) and/or the solubility of the active agent. When the beneficial agent is poorly soluble in water and has a low diffusivity, the aqueous suspension of the active agent composition of layer (3) is mainly released to the environment of use across the at least one passageway (5) of the wall in a controlled manner over a prolonged period of time. In the case of water soluble active agents, the increase in concentration of the active agent in the solution adjacent the membrane (4) will effect release of the active agent by diffusion. Additionally, the swelling of the expandable hydrophilic polymer core contributes to the complete release of the solution at a substantially steady rate, minimizing diffusional resistance of the boundary layer.

As used herein, the terms "very soluble", "freely soluble", "soluble", "sparingly soluble", "slightly soluble", "very slightly soluble", and "practically insoluble" or "insoluble" are defined as they are defined in the U.S.P. $23^{rd}$ Ed. as follows:

| Term | Solubility of component in water (parts of solvent per part of component) |
|---|---|
| Very soluble | <1 |
| Freely soluble | 1–10 |
| Soluble | 10–30 |
| Sparingly soluble | 30–100 |
| Slightly soluble | 100–1,000 |
| Very slightly soluble | 1,000–10,000 |
| Practically insoluble or insoluble | Over 10,000 |

The formulation of the present delivery device can be changed according to the following guidelines to permit delivery of slightly, sparingly and very soluble active agents. The following guidelines are applicable to embodiments of the delivery device intended for use in an aqueous environment.

For slightly water soluble active agents, such as allopurinol, amoxicilin, aspirin, cefazolin, cimetidine, hydrochlorothiazide, nifedipine, and cisapride monohydrate, the active agent is mostly delivered through the preformed passageway. The core can comprise an expandable hydrophilic polymer, such as HPMC, methylcellulose (MC), carboxymethylcellulose sodium (CMC—Na), and poly (alkylene oxides), and/or an osmagent, such as NaCl, mannitol, dextrose, sodium tartrate, and sodium acetate. The layer surrounding and in contact with the core can comprise the active substance, an osmopolymer, and an osmagent. The wall surrounding and in contact with the layer containing active agent can comprise a cellulose ester, such as cellulose acetate, cellulose propionate, and cellulose acetate-butyrate, a polymethacrylate copolymer, such as poly (ammonium methacrylate) copolymer and (ethyl acrylate)-(methyl methacrylate)-[(trimethylammonium)ethyl methacrylate], and a plasticizer, such as PEG 400, PEG 6000, triacetin and glycerin. The cellulose ester, polymethacrylate copolymer and plasticizer are generally present in the ratio of 0.1–99.8 wt. cellulose ester: 0.1–99.8% wt. polymethacrylate copolymer: 0.1–25% plasticizer. For very water soluble active agents, such as meperidine HCl, buspirone HCl, diltiazem HCl, oxybutynin HCl, ranitidine HCl, pseudoephedrine HCl, and venlafaxine HCl, the active agent is delivered through both the preformed passageway and the micropores of the wall. The core can comprise a hydrophilic expandable polymer and an osmagent. The layer surrounding and in contact with the core can comprise the active substance, and a hydrophilic expandable polymer and an osmagent. The wall surrounding and in contact with the layer containing active substance generally comprise a cellulose ester, a poly(methacrylate) copolymer, and a plasticizer.

For sparingly water soluble active substances, such as caffeine, ciprofloxacin HCl, enalapril maleate, and metronidazole, the active agent is delivered through both the preformed passageway and the micropores of the wall. The core can comprise an expandable hydrophilic polymer, and an osmagent, such as. The layer surrounding and in contact with the core can comprise the active substance, an osmopolymer and an osmagent. The wall surrounding and in contact with the layer containing active agent can comprise a cellulose ester, a polymethacrylate copolymer, and a plasticizer. The cellulose ester, polymethacrylate copolymer and plasticizer are generally present in the ratio of 0.1–99.8% wt. cellulose ester: 0.1–99.8% wt. polymethacrylate copolymer: 0.1–25% plasticizer.

The micropores in the wall are not formed by mechanical means. The micropores are formed during preparation of the wall or during exposure to fluids in an intended environment of use. Methods of preparing walls wherein the micropores form in the environment of use are well known and described in, among others, U.S. Pat. Nos. 3,845,770, 3,916,899, 4,063,064, 4,088,864, 4,816,263, 4,200,098, 4,285,987 and No. 5,912,268, the relevant disclosures of which are hereby incorporated by reference.

Swellable hydrophilic polymers suitable for manufacturing the core (2) include hydrophilic polymers that interact with water and/or aqueous biological fluids, and swell and retain water within their structure. The core preferably expands to about 2 to 50 times its initial volume. The polymers are preferably slightly cross-linked. Uncrosslinked polymers will preferably not dissolve in water, keeping their physical integrity. The polymers are of animal, plant or synthetic origin. Hydrophilic polymers suitable for manufacturing the core of the invention preferably include hydroxypropyl methylcelluloses (viscosity from 3 to 100,000 cps, measured in 2% w/v solution); ethylcelluloses (viscosity from 3 to 110 cP, measured in 5% w/v solution); methylcelluloses (viscosity from 10 to 10,000 cP, measured in 2% w/v solution); hydroxypropylcelluloses (general average molecular weight of about 80,000 to 1,150,000); hydroxyethylcelluloses (viscosity from 2 to 21,000 cP, measured in 2% w/v solution); carboxymethylcelluloses (viscosity from 5 to 4,000 cP, measured in 1% w/v solution); poly (alkylene) oxide that might include homopolymer of ethylene oxide, propylene oxide and butylene oxide and copolymers of those.

The poly(alkylene oxides) used herein preferably have an average molecular weight of about 1,000,000 to 2,000,000 (viscosity around 400–800 and 2,000–4,000 cP, measured in 2% w/v solution), or an average molecular weight around 4,000,000 to 8,000,000 (viscosity around 1,650–5,500 and 10,000–15,000 cP, measured in 1% w/v solution).

The membrane, or wall, (4) according to the invention preferably comprises a mixture of cellulose esters (CE), copolymers of methacrylate salts (CM) and a plasticizer (P). The active agent is released in a controlled manner through the membrane (4) by the combined mechanisms of diffusion and osmotic pumping. The ratio CE:CM:P is preferably about 1–99% of CE: about 84–0.5% of CM weight: about 15–0.5% of P by weight. The ratio of these ingredients is varied to control delivery of active agents either predominantly by diffusion across the surface of the membrane (4) to predominantly by osmotic pumping through the passageway (5) and combinations thereof.

Representative cellulose esters useful in the membrane of the invention include cellulose acylate; mono, di and tricellulose alkanylates; mono, di and tricellulose aroylates; cellulose propionate; cellulose acetate-butyrate; cellulose triacylates such as cellulose trivalerate, cellulose trilaurate, cellulose tripalmitate, cellulose trisuccinate; cellulose diacylates such as cellulose disuccinate, cellulose dipalmitate; combinations thereof and other cellulose esters used by those of ordinary skill in the art in the preparation of controlled delivery devices and membranes.

The poly(methacrylate) copolymer salts used in the manufacturing of the membrane (4) are preferably insoluble in water and in digestive fluids, but films made therefrom are preferably permeable to dissolved substances to different degrees. Preferred copolymers include: poly(ammonium methacrylate) copolymer RL (Eudragit™ RL), poly (ammonium methacrylate) copolymer (type A-USP/NF), poly(aminoalkyl methacrylate) copolymer RL-JSP I), and (ethyl acrylate)-(methyl methacrylate)-[(trimethylammonium)-ethylmethacrylate] (1:2:0.2) copolymer, MW 150,000. More preferred polymers include (Röhm Pharma, Weiterstadt): Eudragit™ RS 100: solid polymer, Eudragit™ RL 12.5:12.5% solution in solvent, Eudragit™ RL 30 D: 30% aqueous dispersion, and other equivalent products.

The following poly (ammonium methacrylate) copolymers can also be used: ammonium methacrylate copolymer RS (Eudragit™ RS), poly(ammonium methacrylate) copolymer (type B-USP/NF), poly(aminoalkyl methacrylate) copolymer (RSL-JSP I), (ethyl acrylate)-(methyl methacrylate)-[(trimethylammonium)-ethyl methacrylate] (1:2:0.1) copolymer, PM 150,000. Specific polymers include (Röhm Pharma, Weiterstadt): Eudragit™ RS 100: solid polymer, Eudragit™ RS 12.5: 12.5% solution in solvent, Eudragit™ RS 30 D: 30% aqueous dispersion and other equivalent products. Eudragit™ RL is readily water permeable while Eudragit™ RS is hardly water permeable. By employing mixtures of both Eudragit™ RL and Eudragit™ RS, membranes having the desired degree of permeability are prepared.

The porosity of the wall will vary according to its composition. A highly porous wall is preferably used to deliver slightly soluble active substances. A highly porous wall will provide a faster release of drug than a slightly porous wall. A slightly porous wall is generally used to deliver very soluble active substances. A moderately porous wall is generally used to deliver moderately soluble active substances. A moderately porous wall will provide a faster release of drug than a slightly porous wall.

Plasticizers that can be used in the membrane of the invention include all those that are generally incorporated into polymeric coatings of delivery devices. Plasticizers generally improve the mechanical properties and increase the flexibility of the polymeric film. Plasticizers generally reduce cohesive intermolecular forces and increase mobility of polymer chains, thus reducing polymer-polymer interactions. This action is responsible for the changes to the properties of the polymers and films thereof such as a reduction of Tg (glass transition temperature) or softening temperature and the elastic module, increasing polymer flexibility, thus facilitating the process of formation of the membrane or film. A preferred pharmaceutical plasticizer is non-toxic and non-irritating; has a reduced tendency to migrate, extrude or volatilize; and has good miscibility with the polymers in film. Plasticizers that are used in the wall of the present invention include, for example, acetyl triethyl citrate, acetyl tributyl citrate, triethyl citrate, acetylated monoglycerides, glycerol, polyethylene glycol, triacetin, propylene glycol, dibutyl phthalate, diethyl phthalate, isopropyl phthalate, dimethyl phthalate, dactyl phthalate, dibutyl sebacate, dimethyl sebacate, castor oil, glycerol monostearate, fractionated coconut oil, and others. Preferably, polyethylene glycol is used, for example PEG 400, which is available from suppliers such as Aldrich, Sigma Chemical Co. and others.

Suitable plasticizers also include, by way of example and without limitation, low molecular weight polymers, oligomers, copolymers, oils, small organic molecules, low molecular weight polyols having aliphatic hydroxyls, ester-type plasticizers, glycol esters, poly(propylene glycol), multi-block polymers, single-block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. A combination of plasticizers may also be used in the present formulation. The PEG based plasticizers are commercially available or can be made by a variety of methods, such as disclosed in Poly (*ethylene glycol*) *Chemistry: Biotechnical and Biomedical Applications* (J. M. Harris, Ed.; Plenum Press, NY) the disclosure of which is hereby incorporated by reference.

The passageway (5) in the membrane (4) that connects the inside of the delivery device (1) with the outside allows release of the active agent to the environment of use. Exemplary passageways include an orifice, hole, bore, aperture or the like, through which the active agent is released. Mechanical perforation, laser perforation or any other method known to the artisan of ordinary skill in the art is used to form the passageway. Although the osmotic device (1) is depicted with a single passageway (5), a device according to the present invention can comprise one or more passageways including two, three, four, five, six, seven, eight, nine, ten or more passageways. The one or more passageway/s are formed in any place of the delivery device. The maximum and minimum dimensions of the passageway are preferably as disclosed in U.S. Pat. No. 3,845,770 (AR 199,301).

The device of the present invention can, optionally, include an external coating comprising an active agent for immediate, rapid, slow, sustained, extended, controlled or delayed delivery to the environment of use. Useful materials for the external coating include poly(vinylpyrrolidone) (PVP), poly(ethylene glycol) (PEG), hydroxypropyl ethylcellulose, hydroxypropyl methylcellulose, ethylcellulose, hydroxyethylcellulose, sodium carboxymethyl cellulose, dimethylaminoethyl methalcrylate-methalcrylate acid ester copolymer, soluble polysaccharide gums such as carrageenan, tragacanth, pectin, guar, combinations thereof and other such materials known by those of ordinary skill in the art. The external layer is dissolved, eroded or completely removed in the environment of use and provides an immediate delivery of the active agent to the environment of use. The active agent comprises about 0.1 to 99.9% by weight of the external coating.

The layer (3) depicted in FIG. 1-*a* includes a composition comprising an active agent and optionally other materials as discussed herein. The quantity of active agent may vary between 0.10 and 99.9% by weight of the layer (3). The preferred amount of active agent in the layer (3) may vary according to the active agent employed.

Osmotically effective compounds, such as osmotic agents or osmagents, that are capable of being totally or partially solubilized in the fluid may be added to the layer (3). Osmagents or osmotically effective compounds are generally soluble in the fluid that enters into the device through the wall (4) creating an osmotic pressure gradient across the wall. The fluid and components of the layer (3) will generally form a solution or suspension comprising the active agent to be delivered. Exemplary osmagents include high or low molecular weight compounds, organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials known to those of ordinary skill in the art. Preferred osmagents include potassium chloride, sodium tartrate, glucose, mannitol, sodium acetate, sodium chloride, sodium sulfate, sodium citrate, potassium tartrate, sorbitol, sucrose and combinations thereof.

The layer (3) comprising the active agent can also comprise an osmopolymer such as the ones previously described for the core (2), preferably poly(alkylene oxide) and, more preferably, poly(ethylene oxide) with an average molecular weight between about 100,000 and 8,000,000.

The delivery device of the invention advantageously requires lower amounts of osmagent, osmopolymer or osmotically effective agent to deliver an active substance than is required by related osmotic devices containing the same amount of active substance. Accordingly, the present delivery device contains a higher relative loading of active substance than other comparable osmotic devices containing the same absolute amount of active substance, and is generally smaller and lighter than such other devices. In preferred embodiments, the percentage of active substance present in the entire device ranges from about 0.1% to about 99% with respect to the total weight of the device.

The delivery device of the invention can also comprise adsorbents, acidifying agents, alkalizing agents, antioxidants, buffering agents, colorants, flavorants, sweetening agents, antiadherents, binders, diluents, direct compression excipients, disintegrants, tablet glidants, tablet or capsule opaquants and/or tablet polishing agents.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "acidifying agent" is intended to mean a compound used to provide an acidic medium for product stability. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other such materials known to those of ordinary skill in the art.

As used herein, the term "antioxidant" is intended to mean an agent who inhibits oxidation and is thus used to prevent the deterioration of preparations by the oxidative process. Such compounds include, by way of example and without limitation, ascorbic acid, ascorbic palmitate, Vitamin E, butylated hydroxyanisole, butylated hydroxytoluene, hypophosphorous acid, monothioglycerol, propyl gallate, sodium ascorbate, sodium bisulfite, sodium formaldehyde sulfoxylate, sodium metalbisulfite and other such materials known to those of ordinary skill in the art.

As used herein, the term "buffering agent" is intended to mean a compound used to resist a change in pH upon dilution or addition of acid or alkali. Such compounds include, by way of example and without limitation, potassium metaphosphate, potassium phosphate, monobasic sodium acetate and sodium citrate anhydrous and dehydrate and other such materials known to those of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol, sucrose, fructose and other such materials known to those of ordinary skill in the art.

As used herein, the expression "antiadherents" is intended to mean agents that prevent the sticking of tablet formulation ingredients to the punches and dies in a tableting machine during production. Such compounds include, by way of example and without limitation, magnesium stearate, calcium stearate, talc, glyceryl behenate, poly(ethylene glycol), hydrogenated vegetable oil, mineral oil, stearic acid, combinations thereof and other such materials known to those of ordinary skill in the art.

As used herein, the term "binders" is intended to mean substances used to cause adhesion of powder particles in tablet granulations. Such compounds include, by way of example and without limitation, acacia, alginic acid, tragacanth, carboxymethylcellulose sodium, poly(vinylpyrrolidone), compressible sugar (e.g., NuTab), ethylcellulose, gelatin, liquid glucose, methylcellulose, povidone and pregelatinized starch, combinations thereof and other materials known to those of ordinary skill in the art.

When needed, other binders may also be included in the present osmotic device. Exemplary binders include starch, poly(ethylene glycol), guar gum, polysaccharide, bentonites, sugars, invert sugars, poloxamers (PLURONIC™ F68, PLURONIC™ F127), collagen, albumin, celluloses in non-aqueous solvents, combinations thereof and the like. Other binders include, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

As used herein, the term "tablet direct compression excipient" is intended to mean a compound used in direct compression tablet formulations. Such compounds include, by way of example and without limitation, dibasic calcium phosphate (e.g. Ditab™), microcrystalline cellulose, direct compression lactose (e.g. Tablettose™, Lactose DT) combinations thereof and other such materials known to those of ordinary skill in the art.

As used herein, the term "glidant" is intended to mean agents used in tablet and capsule formulations to improve flow-properties during tablet compression and to produce an anti caking effect. Such compounds include, by way of example and without limitation, colloidal silica, calcium silicate, magnesium silicate, silicon hydrogel, cornstarch, talc, combinations thereof and other such materials known to those of ordinary skill in the art.

As used herein, the term "lubricant" is intended to mean substances used in tablet formulations to reduce friction during tablet compression. Such compounds include, by way of example and without limitation, calcium stearate, magnesium stearate, mineral oil, stearic acid, zinc stearate, combinations thereof and other such materials known to those of ordinary skill in the art.

As used herein, the term "tablet/capsule opaquant" is intended to mean a compound used to used in tablet coatings or capsules providing useful opacity which can aid the stability to the light in case of sensitive agents. It may be used alone or in combination with a colorant. Such compounds include, by way of example and without limitation, titanium dioxide and other such materials known to those of ordinary skill in the art.

As used herein, the term "tablet polishing agent" is intended to mean a compound used to impart brightness to the surface of the coated tablets. Such compounds include, by way of example and without limitation, carnauba wax, white wax, combinations thereof and other such materials known to those of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g. Avicel™), carboxymethylcellulose calcium, cellulose polyacrylin potassium (e.g. Amberlite™), alginates, sodium starch glycolate, gums such as agar, guar, locust bean, karaya, pectin, tragacanth, combinations thereof and other such materials known to those of ordinary skill in the art.

As used herein, the term "colorant" is intended to mean a compound used to impart color to pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and iron oxide (black, red, yellow), other F.D. & C. dyes and natural coloring agents such as grape skin extract, beet red powder, beta-carotene, annato, carmine, turmeric, paprika, combinations thereof and other such materials known to those of ordinary skill in the art.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors, which have been found to be particularly useful, include commercially available orange, grape, cherry and bubble gum flavors and mixtures thereof. The amount of flavoring may depend on a number of factors, including the desired organoleptic effect. Flavors will be present in any amount as desired by the artisan of ordinary skill in the art. Particularly preferred flavors are the grape and cherry flavors and citrus flavors such as orange.

The delivery device of the invention can also include oils such as fixed oils, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides and acetylated fatty acid glycerides. The device can also include alcohol such as ethanol, isopropanol, hexadecyl alcohol, glycerol and propylene glycol; glycerol ketals such as 2,2-dimethyl-1,3-dioxolane-4-methanol; ethers such as poly (ethyleneglycol) 450; petroleum hydrocarbons such as mineral oil and petrolatum; water; mixtures thereof; or a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents such as dimethyl dialkyl ammonium halides, alkyl pyridinium halides, and alkylamine acetates; anionic detergents such as alkyl, aryl and olefin sulfonates, alkyl, olefin, ether and monoglyceride sulfates, and sulfosuccinates; non-ionic detergents such as fatty amine oxides, fatty acid alkanolamides, and poly(oxyethylene)-block-poly (oxypropylene) copolymers; amphoteric detergents such as alkyl β-aminopropionates and 2-alkylimidazoline quaternary ammonium salts; and mixtures thereof.

Various other components, not otherwise listed above, can be added to the present formulation to provide a device with a desired release profile. Such components include, by way of example and without limitation, glycerylmonostearate, nylon, cellulose acetate butyrate, d,l-poly (lactic acid), 1,6-hexanediamine, diethylenetriamine, starches, derivatized starches, acetylated monoglycerides, gelatin coacervates, poly(styrene-maleic acid) copolymer, glycowax, castor wax, stearyl alcohol, glycerol palmitostearate, poly ethylene, poly (vinyl acetate), poly(vinyl chloride), 1,3-butyleneglycoldimethacrylate, ethyleneglycol-dimethacrylate and methacrylate hydrogels.

It should be understood that the compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

Active agents preferably include physiologically or pharmacologically active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleaning, confectionery and flavoring applications. The active agent can be present in its neutral, ionic, salt, basic, acidic, natural, synthetic, diastereometric, isomeric, enantiomerically pure, racemic, hydrate, chelate, derivative, analog, or other common form.

The drug delivery device of the invention can be used to deliver two or more different active agents. Particular combinations of active agents can be provided by the present delivery device. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; 4) a first drug having a first type of biological activity and a different second drug having a different second type of biological activity. Exemplary combinations of active agents are described herein. The active agents can be delivered to the same or different environments of use. Accordingly, the active agent can be independently selected at each occurrence from therapeutic compounds such as an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, antidepressant agent, antidiabetic agent, antineoplastic agent, antipsychotic agent, neuroleptic agent, antihypertensive agent, hypnotic agent, sedative agent, anxiolytic energizer agent, antiparkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, anti-ulcerant agent, anti-flatulent agent, anti-incontinence agent, cardiovascular agent or a combination thereof.

Representative antibacterial substances include, for example, penicillins: penicillin G and V, penicillinase-resistant penicillin (methicillin, nafcillin, oxacilin, cloxacilin and dicloxacillin), and aminopenicillins: ampicillin, amoxicillin, cyclacillin; carboxy and ureidopenicillines such as carbenicillin, ticarcillin, azlocillin, mezlocillin and piperacilllin; cephalosporins such as the first-generation cephalosporins such as cephalotin, cephalexin, cefazolin, second generation cephalosporins such as cefoxitin, cefaclor, cefuroxime, and third generation cephalosporins such as cefotaxime, ceftriaxone, ceftazidime; beta-lactam antibiotics such as imipenem, aztreonam; sulfonamides such as sulfisoxazole, sulfamethoxazole, sulfadiazine, sulfasalazine and trimethropim-sulfamethoxazole; tetracyclines such as oxytetracycline, methacycline, chlorotetracycline and doxycycline; chloramphenicol, erythromycin, lincomycin, clindamycin, vancomycin, bacitracin; aminoglycoside antiobiotics such as streptomycin, gentamicin, tobramycin, amikacin, kanamycin and neomycin; and quinolones such as nalidixic acid, norfloxacin, ciprofloxacin, cinoxacin, ofloxacin, enoxacin, lomefloxacin, amifloxacin and pefloxacin.

Representative antiparasitic compounds include anthelmintics such as ivermectin, mebendazole, albendazole, piperazine, praziquantel, thiabendazole, and dapsone. Representative anti-malarial compounds include chloroquine and its congeners, diaminopyrimidines, mefloquine, primaquine and pyrimethamine. Miscellaneous antiparasitic agents include 8-hydroxyquinolines, metronidazole, quinacrine and paromomycin.

Representative antiviral compounds include acyclovir, gancyclovir, zanamivir, oseltamivir, GS 4104, 2,3-didehydro-2,4-dideoxy-4-guanidinyl-N-acetylneuraminic acid, GG167 (4-guanidino-2,4-dideoxy-2,3-dehydro-N-acetylneuraminic acid), pencyclovir, RWJ-270201, (+/−)-(2S,3R,4R)-2-(trifluoroacetamido)methyl-3-amino-1-(N'-ethyl-N'-isopropylcarbamyl)pyrrolidine-4-carboxylic acid (A-192558), foscarnet, 6-Acetamido-5-amino- and -5-guanidino-3,4-dehydro-N-(2-ethylbutyryl)-3-piperidinecarboxylic acids, idoxuridine, trifluridine and vidarabine; anti-retroviral compounds such as zidovudine, didadosine, estavudine; others such as interferon, amantadine and rivavirine; neuraminidase inhibitors.

Representative antineoplastics include nitrogen mustards such as mechlorethamine chlorambucil, cyclophosphamide; ethylenimines and methylmelamines such as triethylenemelamine, thiotepa, hexamethyl-melamine; alkyl sulfonates such as busulfan; nitrosureas such as carmustine (BCNU), lomustine; dacarbazine; folic acid analogs such as methotrexate; pyrimidine analogs such as fluorouracil, arabinoside cytisine; purine analogs such as mercaptopurine, azathiprine; vinca alkaloids such as vincristine, vinblastine, taxol; etoposide; antibiotics such as actinomycin D, daunorubicin, doxorubicin, bleomycin, mitomycin; cisplatin; hydroxyurea; procarbazine; aminoglutethimide; cisplatin and tamoxifen.

Representative anti-inflammatory and analgesic drugs include cortisone, hydrocortisone, prednisone, prednisolone, betamethasone, dexamethasone and fluorocortisone; cyclooxygenase II inhibitors such as rofecoxib, celecoxib, flosulide, NS-398, DUP-697, meloxicam, 6-methoxy-2-naphthylacetic acid, nabumetone, etodolac, nimesulide, SC-5766, SC-58215, T-614; salicylates such as salicylic acid, aspirin and diflunisal; pyrazolon derivates such as phenylbutazone and oxyphenbutazone; aminopyridines such as dipyrone, para-aminophenol derivates such as acetaminophen and phenacetin, indomethacin and sulindac; fenamates such as mefenamic acid; tolmetin; propionic acid derivates such as ibuprofen, naproxen, fenoprofen, ketoprofen, flurbiprofen and indoprofen; piroxicam, and diclofenac. Representative opioid analgesics include morphine, codeine, meperidine and nalorphine.

Representative anti-incontinence agents include oxybutynin, tolterodine, and darifenacin.

Representative gastric acid secretion inhibitors include ranitidine and omeprazole, which are known as H2 blocker or acid-suppressing drugs.

Representative drugs used in the treatment of gout include colchicine, allopurinol, probenecid and sulphinpirazone.

Representative antihistamines and decongestants include the first generation compounds such as diphenhydramine, pirilamine, chlorpheniramine, brompheniramine, promethazine; H1 antagonists such as acrivastine, astemizole, azelastine, cetirizine, ebastine, epinastine, fexofenadine, loratadine, mizolastine, norastemizol, prometazine and terfenadine.

Representative sympathomimetic drugs include epinephrine, amphetamine, ephedrine and norepinephrine.

Representative antiasthmatic drugs include methylxanthines such as theophylline; from corticoids such as beclomethasone dipropionate, budesonide, flunisolide, prednisone;

bronchodilators such as albuterol, salbutamol, salmetherol, terbutaline; antimuscharinic agents such as ipratopium bromide; and cromolyn sodium.

Representative local anesthetics include benzocaine, procaine, lidocaine, cocaine, tetracaine, bupivacaine and dibucaine.

Representative muscle relaxants and antispasmodic agents include alcuronium, alosetron, aminophylline, baclofen, carisoprodol, chlorphenesin, chlorphenesin carbamate, chlorzoxazone, chlormezanone, cyclobenzaprine, dantrolene, decamethonium, diazepam, dyphylline, eperisione, ethaverine, gallamine triethiodide, hexafluorenium, mephenesin, metaxalone, methocarbamol, metocurine iodide, orphenadrine, pancuronium, papaverine, pipecuronium, pridinol, succinylcholine, theophylline, tizanidine, tolperisone, tubocurarine, vecuronium, idrocilamide, ligustilide, cnidilide, senkyunolide, baclofen, trihexylphenidyl, pridinol, and biperiden.

Representative antiparkinson disease compounds include levodopa, carbidopa, benceracide, amantadine, bromocriptine and pergolide.

Representative antidepressant compounds include tricyclic agents such as amitriptyline, imipramine, clomipramine, doxepine; monoamine oxidase inhibitors such as isocoboxazid, phenelzine and tranylcypromine; fluoxetine, fluvoxamine, paroxetine, sertraline, alprazolam, venlafaxine, bupropione and trazodone.

Representative anticonvulsants include hydantoins such as phenytoin, barbiturates and deoxy derivates such as phenobarbital and primidone; carbamazepine, ethosuximide, valproic acid; and benzodiacepines such as diazepam and clonazepam.

Representative antipsychotics include risperidone, olanzapine, clozapine, sertindole, ziprasidone, quetiapine, sulpiride, pimozide, clothiapine, molindone, loxapine, trifluoperazine, haloperidol, flupenthixol, chlorpromazine, chlorprothixene, clopenthixol, droperidol, perphenazine, fluphenazine, lithium, mesoridazine, spiperone, promazine, prochlorperazine, thioridazine, thiothixene, triflupromazine and raclopride, and trifluoperazine.

Representative hypnotics and sedatives include barbiturates such as pentobarbital sodium, phenobarbital, secobarbital, thiopental; benzodiazepines such as diazepam, alprazolam, chlordiazepoxide, clonazepam, lorazepam, oxazepam; buspirone, meprobamate, zolpidem and zoplicone.

Representative hypoglucemic agents include insulin, insulin zinc, isophane insulin, protamine zinc insuline and extended insulin zinc suspension; sulfonylureas such as tolbutamide, chlorpropamide, acetohexamide, glyburide, glipizide, glicazide; biguanides such as phenformin, metformin; ciglitazone, troglitazone, and acarbose.

Representative antidiuretics drugs include inhibitors of carbonic anhydrase such as acetazolamide, chortalidone, indapamine; benzothiadiazides such as chlorothiazide, hydrochlorothiazide; ethacrynic acid, furosemide, bumetanide; aldosterone antagonists such as spironolactone; triamtirene and amiloride.

Representative antihypertensive and cardiovascular drugs include inhibitors of the renin-angiotensin system such as enalapril, lisinopril, ramipril, captopril, perindopril, trandolapril; angiotensin II receptors antagonists such as losartan; calcium channel blockers: nifedipine, amlodipine, nitrendipine, nimodipine, diltiazem, verapamil; simpathocolitic agents; adrenergic antagonists; atenolol, propanolol, nadolol, sotalol, timolol, metropolol, acebutolol, carvedilol; adrenergic agonists; prazosin, fentolamine; centrally acting agents such as methyldopa, clonidine, guanfacine, reserpine; direct arterial and venous vasodilators such as sodium nitroprusside, nitroglicerin, isosorbide 5-mononitrate, isosorbide dinitrate; antiarrhythmic agents such as quinidine, procainamide, phenytoin, lidocaine, mexiletine, propafenone, flecainide, encainide, propranolol, acebutolol, amiodarone, sotalol, verapamil and diltiazem; digitalis; and cardiac glycosides such as digoxine, digitoxine, amrinone, and milrinone.

Representative anticoagulants include heparin, warfarin, dicoumarol; thrombolytic agents such as streptokinase, tissue plasminogen activator (t-PA) urokinase and antiplatelet drugs such as dipyridamole, ticlopidine, and sulfinpyrazone.

Representative prokinetic gastrointestinal drugs include cisapride, clevopride, domperidone, metoclopramide and mosapride.

Representative anti-spasmodic and muscle contractants include atropine, scopolamine, methoescopolamine and oxyphenonium.

Representative steroidal drugs include prednisolone, cortisone, cortisol and triamcinolone; androgenic steroids such as methyltesterone, and fluoxmesterone; estrogenic steroids such as 17β-estradiol, α-estradiol, estriol, α-estradiol 3 benzoate, and 17-ethynylestradiol-3-methyl ether; and progestational steroids such as progesterone, 19-nor-pregn-4-ene-3,20-dione, 17-hydroxy-19-nor-17-α-pregn-5(10)-ene-20-yn-3-one, 17α-ethynyl-17-hydroxy-5 (10)-estren-3-one, and 9β, 10α-pregna-4,6-diene-3,20-dione.

Representative ophthalmic agents include pilocarpine, pilocarpine salts such as pilocarpine nitrate, pilocarpine hydrochloride, dichlophenamide, atropine, atropine sulfate, scopolamine and eserine salicylate.

Representative nutritional agents include ascorbic acid, niacin, nicotinamide, folic acid, choline biotin, panthothenic acid, and vitamin B12, essential amino acids, and essential fats.

Representative electrolytes include calcium gluconate, calcium lactate, potassium chloride, potassium sulfate, sodium chloride, sodium fluoride, ferrous lactate, ferrous gluconate, ferrous sulfate, ferrous fumarate and sodium lactate.

The above-mentioned list should not be considered exhaustive and is merely exemplary of the many embodiments considered within the scope of the invention. Many other active compounds can be administered with the device of the present invention.

The therapeutic compound(s) contained within the present device can be formulated as its pharmaceutically acceptable salts. As used herein, "pharmaceutically acceptable salts" refers to derivatives of the disclosed compounds wherein the therapeutic compound is modified by reacting it with an acid or base as needed to form an ionically bound pair. Examples of pharmaceutically acceptable salts include conventional non-toxic salts or the quaternary ammonium salts of the parent compound formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. The pharmaceutically acceptable salts of the present invention can be synthesized from the parent therapeutic compound which contains a basic or acidic moiety by conventional chemical methods. Lists of other suitable salts are found in *Remington's Pharmaceutical Sciences,* 17th. ed., Mack Publishing Company, Easton, Pa., 1985, p. 1418, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

As used in this disclosure, the term vitamin refers to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins and can include thiamin pyrophosphates (TPP), flavin mononucleotide (FMN), and flavin adenine dinucleotive (FAD). Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme B12, lipolysine, 11-cis-retinal, and 1,25-dihydroxycholecalciferol. The term vitamin(s) also includes choline, carnitine, and alpha, beta, and gamma carotene.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium, mixtures thereof and others known to those of ordinary skill in the art.

The term "dietary supplement" as used herein means a substance, which has an appreciable nutritional effect when, administered in small amounts. Dietary supplements include, without limitation, such ingredients as bee pollen, bran, wheat germ, kelp, cod liver oil, ginseng, and fish oils, amino-acids, proteins, plant extracts, plant powder, herbs, herbal extracts and powders, vitamins, minerals, combinations thereof and others known to those of ordinary skill in the art. As will be appreciated, essentially any dietary supplement may be incorporated into the present osmotic device.

The amount of therapeutic compound incorporated in each device of the invention will be at least one or more dosage form and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is enough for the required or desired therapeutic response, or in other words, the amount, which is sufficient to elicit an appreciable biological response when, administered to a patient. The appreciable biological response may occur as a result of administration of single or multiple unit doses of an active substance. Depending upon the active substance used and upon the amount of active substance present in a particular device according to the invention, a unit dose may comprise one or more such devices. As used with reference to a vitamin or mineral, the term "effective amount" means an amount at least about 10% of the United States Recommended Daily Allowance ("RDA") of that particular ingredient for a patient. For example, if an intended ingredient were vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

When combinations of active agents are used, one or both of the active agents can be present in a sub-therapeutic amount. As used herein, a sub-therapeutic amount is that amount of first drug which provides less than a normal therapeutic response in patient to which the first drug is administered in the absence of the second drug of the combination. In other words, the first and second drugs may together provide an enhanced, improved, additive or synergistic therapeutic benefit as compared to the administration of each drug alone, i.e., in the absence of the other drug.

For nasal administration of therapeutic compounds, the device of the invention may be included in a paste, cream or ointment containing the appropriate solvents (such as water, aqueous, nonaqueous, polar, apolar, hydrophobic, hydrophilic and/or combinations thereof) and optionally other compounds (stabilizers, perfumes, antimicrobial agents, antioxidants, pH modifiers, surfactants and/or bioavailability modifiers). Bioavailability enhancers such as alcohols or other compounds that enhance the penetration of the therapeutic compound from the pharmaceutical formulation into the nasal mucosa may be needed to prepare suitable formulations for nasal administration.

For oral, buccal, and sublingual administration, the delivery device may be in the form of a caplet or tablet. For rectal administration, the osmotic device can be included in a suppository or tablet for release of a therapeutic compound into the intestines, sigmoid flexure and/or rectum. For cutaneous, subcutaneous, otic, intraperitoneal, ophthalmic and implant applications, the device is a solid dosage form adapted for such application and is preferably a tablet.

The device of the invention can be prepared according to the methods disclosed herein or those well known in the art. For example, according to a preferred process, the hydrophilic polymer or a mixture thereof is mixed with suitable excipients in solid form, is then moistened and sieved through a screen and dried for several hours in a convection oven. The dried granulate is then screened and mixed with other suitable excipients and the homogeneous mixture is subsequently compressed to form 4 to 10 mm diameter expandable placebo cores. A mixture comprising an active agent and a suitable excipient is then compressed over the core (2) to form 6 to 12 mm diameter uncoated tablets. Uncoated tablets are then covered preferably with a mixture of selected polymers that constitute the wall (4). Subsequently, the wall (4) is perforated at any location with a laser, drill or other mechanical means known to those of ordinary skill in the art. Optionally, the tablets may be further coated with an external film comprising an active agent for immediate or sustained delivery to the environment of use.

If desired, the device of the invention can be coated with a finish coating as is commonly done in the art to provide the desired shine, color, taste or other aesthetic characteristics. Materials suitable for preparing the finish coating are well known to those of ordinary skill in the art.

The following examples should not be considered exhaustive, but merely illustrative of only a few of the many embodiments included within the scope of the present invention. The methods described herein can be followed to prepare delivery devices according to the invention.

EXAMPLE 1

Biconvex-shaped expandable cores about 7.0 mm in diameter were prepared without active agent as follows. 20.85 g of lactose monohydrate, 18.25 g of hydroxypropyl methylcellulose (HPMC; 2208 type; Dow Chemical U.S.A.); 1.8 g of poly(ethylene oxide) (4,000,000 molecular weight), 2.15 g of poly(vinylpyrrolidone), 0.30 g of red ferric oxide, and 0.45 g of silicon dioxide were mixed then sieved through a 40-mesh screen. Alcohol (96°, 30 ml) was slowly added to the dry blend until a wet blend was achieved. The wet blend was then sieved through a 10-mesh screen and the granular mass obtained was dried for several hours at 45° C. in a convection oven. The dried granulate was then sieved through a 20-mesh screen. The sieved granulate was mixed with 0.75 g of magnesium stearate and 0.45 g of silicon dioxide (both having been previously sieved through a 60-mesh screen) and then mixed in a V-blender for 5 minutes. The homogeneous mixture was subsequently compressed to form biconvex cores, which individually weighed 90.0 mg.

A first layer comprising the active agent was prepared as follows 20.75 g of cisapride monohydrate, 28.15 g of microcrystalline cellulose, 37.50 g. of sodium chloride, 45.00 g of poly(ethylene oxide) (200,000 molecular weight), 0.37 g of colloidal silicon dioxide and 15.75 g of poly (vinylpyrrolidone) were mixed and then sieved through a 40-mesh screen. The sieved mixture was then granulated with alcohol (96°, 40 ml having 0.85 g of polysorbate 20 previously dissolved in it). All the ingredients were mixed for a few additional minutes. The granular mass was then dried for several hours at 45° C. in a convection oven. Dried granulate was then sieved through a 20 mesh screen. The sieved mixture was mixed with 1.25 g of magnesium stearate and 0.38 g of colloidal silicon dioxide (both previously sieved through a 60 mesh screen) in a V-blender for 5 minutes to form a homogeneous drug-containing composition. The drug-containing composition was compressed about the previously formed expandable cores to form biconvex uncoated cores, about 9.25 mm in diameter, each weighing about 390 mg.

A wall for covering the uncoated cores was prepared as follows. A polymeric suspension was prepared by dissolving 27.36 g of cellulose acetate (average molecular weight 40,000, acetyl content 32% by weight CA), 6.84 g of ammonium methacrylate copolymer (Eudragit™ RS 100, Röhm Pharma) and, 5 weight percent poly(ethylene glycol)), in a mixture of methylene chloride-methyl alcohol 80:20 v/v. The polymeric suspension was then sprayed onto the uncoated tablets to form coated tablets having a wall weighing about 31.63 mg. Two 0.75-mm holes were drilled through the coating in both faces of the device to form a delivery device according to the invention.

Figure 2:
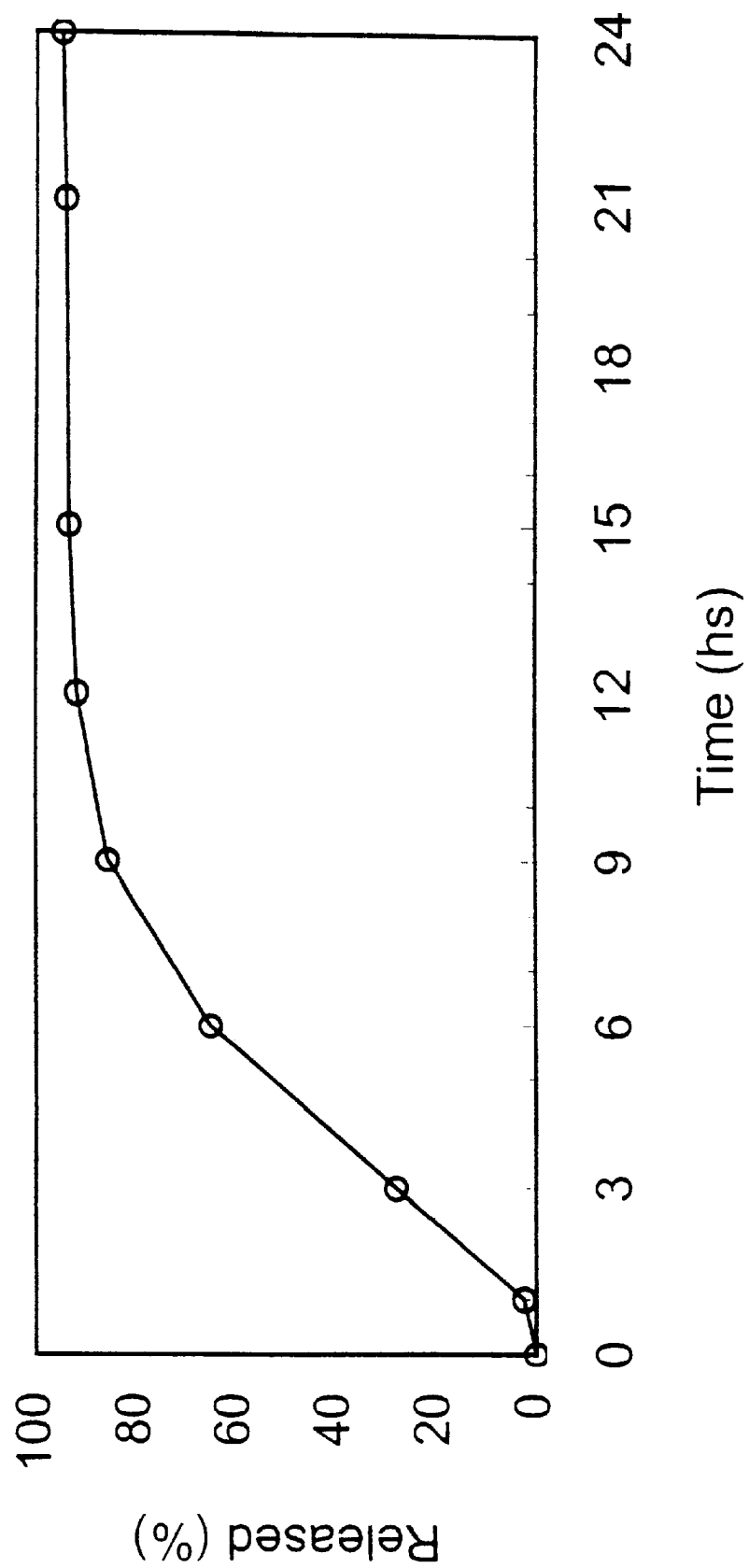
FIGS. 2 to 4 depict active agent release diagrams using the devices of the present invention.

FIG. 2 discloses the results of a drug delivery assay performed on the delivery device in a USP type 3 Apparatus, in distilled water (250 ml, 30 DPM at 37° C.). The release data are summarized in the table below.

| Hours | Accumulative Amount Released (%) |
|---|---|
| 1 | 2.4 |
| 3 | 27.8 |
| 6 | 64.8 |
| 9 | 85.6 |
| 12 | 91.7 |
| 15 | 93.3 |
| 21 | 94.0 |
| 24 | 94.7 |

EXAMPLE 2

Biconvex-shaped cores of 8.0 mm in diameter were prepared without active agent as follows. 21.50 g of hydroxypropyl methylcellulose (HPMC; 2208 type), 23.75 g of poly(ethylene oxide) (300,000 molecular weight), 2.71 g of poly(vinylpyrrolidone), 0.35 g of red ferric oxide, and 0.53 g of silicon dioxide were mixed and sieved through a 40-mesh screen. Then, alcohol (96°; 40 ml) was slowly added to the dry blend to form a wet blend which was sieved through a 10-mesh screen. The resulting granular mass was dried for several hours at 45° C. in a conventional oven, and then sieved through a 20-mesh screen. The granulate was mixed with 0.88 g of magnesium stearate and 0.53 g of silicon dioxide (both after having been sieved through a 60 mesh screen) in a V-blender for 5 minutes. The homogeneous mixture was subsequently compressed to form biconvex cores, which weighed about 100. mg each.

A first layer comprising the active agent was prepared as follows. 16.50 g of micronized nifedipine, 15.00 g of microcrystalline cellulose, 32.05 g of sodium chloride, 37.50 g of poly(ethylene oxide) (200,000 molecular weight), 0.75 g of colloidal silicon dioxide and 19.25 g of poly (vinylpyrrolidone) were mixed and sieved through a 40 mesh screen. The sieved mixture was granulated with alcohol (96°; 35 having 0.70 g of polysorbate 20 previously dissolved in it). All the ingredients were mixed for a few additional minutes. The granular mass was dried for several hours at 45° C. in a convection oven, and the dried granulate was sieved through a 20-mesh screen. The sieved blend was then mixed with 1.75 g of magnesium stearate and 0.75 g of colloidal silicon dioxide (both having been previously sieved through a 60-mesh screen) in a V-blender for 5 minutes. The homogeneous mixture was subsequently compressed about the expandable cores to form biconvex dosage units of about 10 mm in diameter to form the coated device core. The average weight of the cores was about 360 mg.

A wall surrounding the uncoated core was prepared as follows. A polymer suspension was prepared by dissolving 13.3 mg of cellulose acetate (average molecular weight 40,000, acetyl content 32% by weight CA), 13.3 mg of cellulose acetate (average molecular weight 38,000, acetyl content 39.8% by weight CA), 6.65 g of ammonium methacrylate copolymer (Eudragit™ RS 100, Röhm Pharma) and 1.75 g of poly(ethylene glycol), in a mixture of methylene chloride-methyl alcohol 80:20 v/v (493/123 ml). The polymeric mixture was sprayed onto the dosage units to form coated tablets each having a wall weighing about 35 mg. Two 0.75-mm holes were then drilled through the wall, one on each face of the device.

Figure 3:
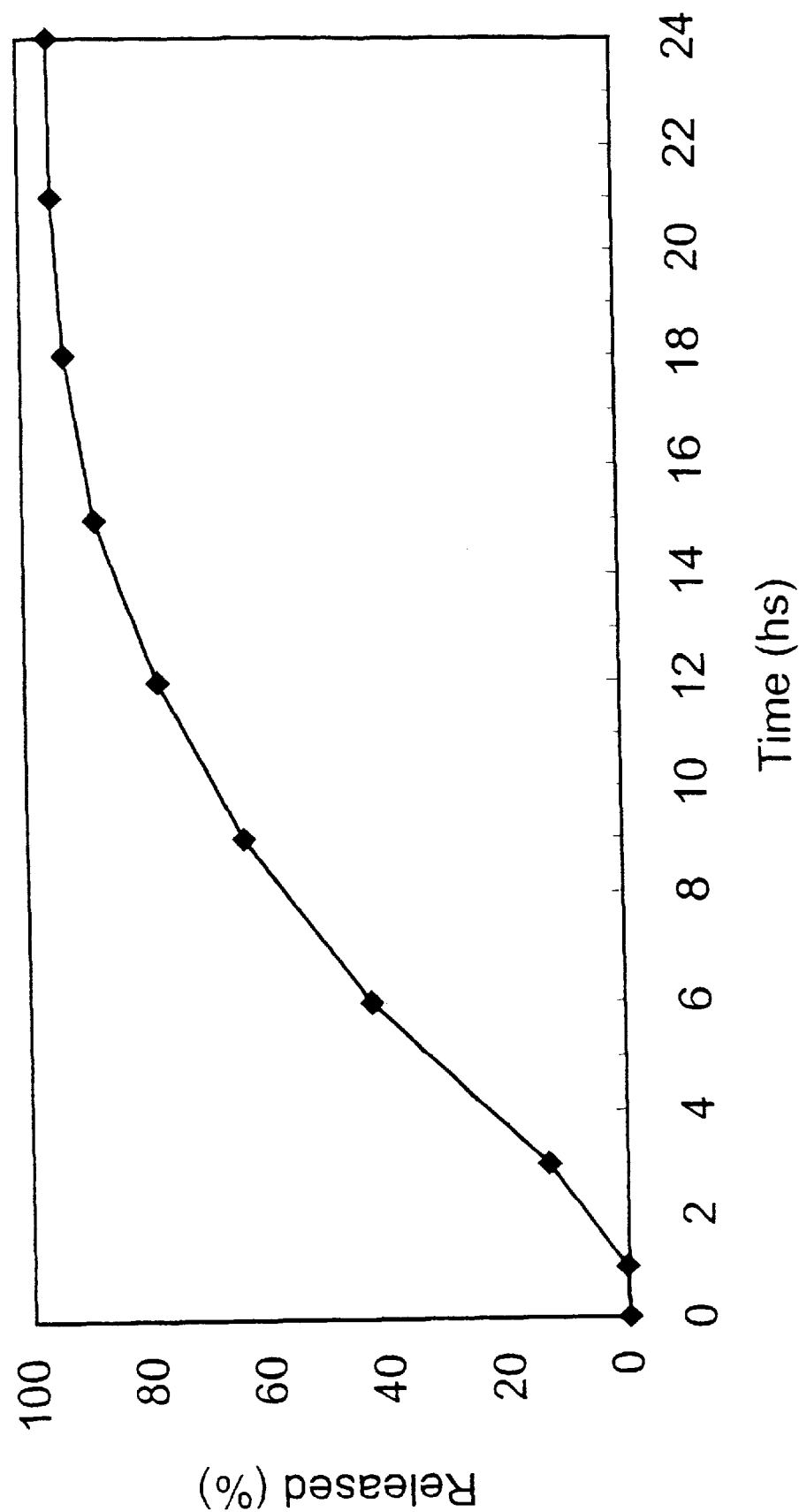

FIG. 3 depicts the release profile for the tablets of this example. The release profile was determined in a USP type 3 Apparatus, in distilled water (250 ml., 30 DPM at 37° C.).

The actual release data obtained are summarized below.

| Hours | Accumulative Amount Released (%) |
|---|---|
| 1 | 0.4 |
| 3 | 13.4 |
| 6 | 42.6 |
| 9 | 63.6 |
| 12 | 77.7 |
| 15 | 87.9 |
| 21 | 94.5 |
| 24 | 94.8 |

EXAMPLE 3

Biconvex-shaped expandable cores about 7 mm in diameter were prepared as follows. 20.85 g of lactose monohydrate, 18.25 g of hydroxypropyl methylcellulose (HPMC, 2208 type), 1.8 g of poly(ethylene oxide) (4,000,000 molecular weight), 2.15 g of poly(vinylpyrrolidone), 0.30 g of red ferric oxide as coloring agent and 0.45 g of silicon dioxide were mixed, and the mix was sieved through a 40-mesh screen. Then, alcohol (96°; 30 ml) was slowly added to the dry blend until a wet blend was achieved. The wet blend was then sieved through a 10 mesh screen and the resulting granulate was dried in a convection oven for several hours. The dried granulate was sieved through a 20-mesh screen and mixed with 0.75 g magnesium stearate and 0.45 g silicon dioxide (both having been previously sieved through a 60-mesh screen) in a V-blender for 5 minutes. The homogeneous mixture was subsequently compressed to form biconvex cores each weighing about 90 mg.

A first layer containing the active agent was prepared as follows. 42.43 g of venlafaxine hydrochloride, 25.22 g of microcrystalline cellulose, 37.5 g of sodium chloride, 45 g of poly(ethylene oxide) (200,000 molecular weight), 0.35 g of colloidal silicon dioxide and 12.00 g of poly (vinylpyrrolidone) were mixed. The blend was sieved through a 40-mesh screen. This mixture was granulated with alcohol (96°; 40 ml, having 0.85 g of polysorbate 20 previously dissolved in it). All the ingredients were mixed for a few additional minutes. The granular mass was dried for several hours at 45° C. in a convection oven. Then the dry granulate was sieved through a 20-mesh screen. The sieved blend was mixed with 1.25 g of magnesium stearate and 0.40 g of colloidal silicon dioxide (having both been previously sieved through a 60 mesh screen) in a V-blender for 5 minutes. The homogeneous mixture was subsequently compressed about the expandable cores to form biconvex-shaped uncoated cores about 9.25 mm in diameter, each weighing about 330 mg.

A wall for covering the uncoated cores was prepared as follows. A polymer suspension was prepared by dissolving 27.36 g of cellulose acetate (average molecular weight 40,000, acetyl content 32% by weight CA), 6.84 g of ammonium methacrylate copolymer (Eudragit™ RS 100, Röhm Pharma) and 1.84 g of poly(ethylene glycol), in a methylene chloride-methyl alcohol mixture of about 80:20 v/v (493 ml/123 ml). This polymer mixture was sprayed onto the uncoated cores to form coated cores, each having a wall weighing about 32.3 mg. Two 0.75-mm holes were drilled through the coating on both faces of the device.

Figure 4:
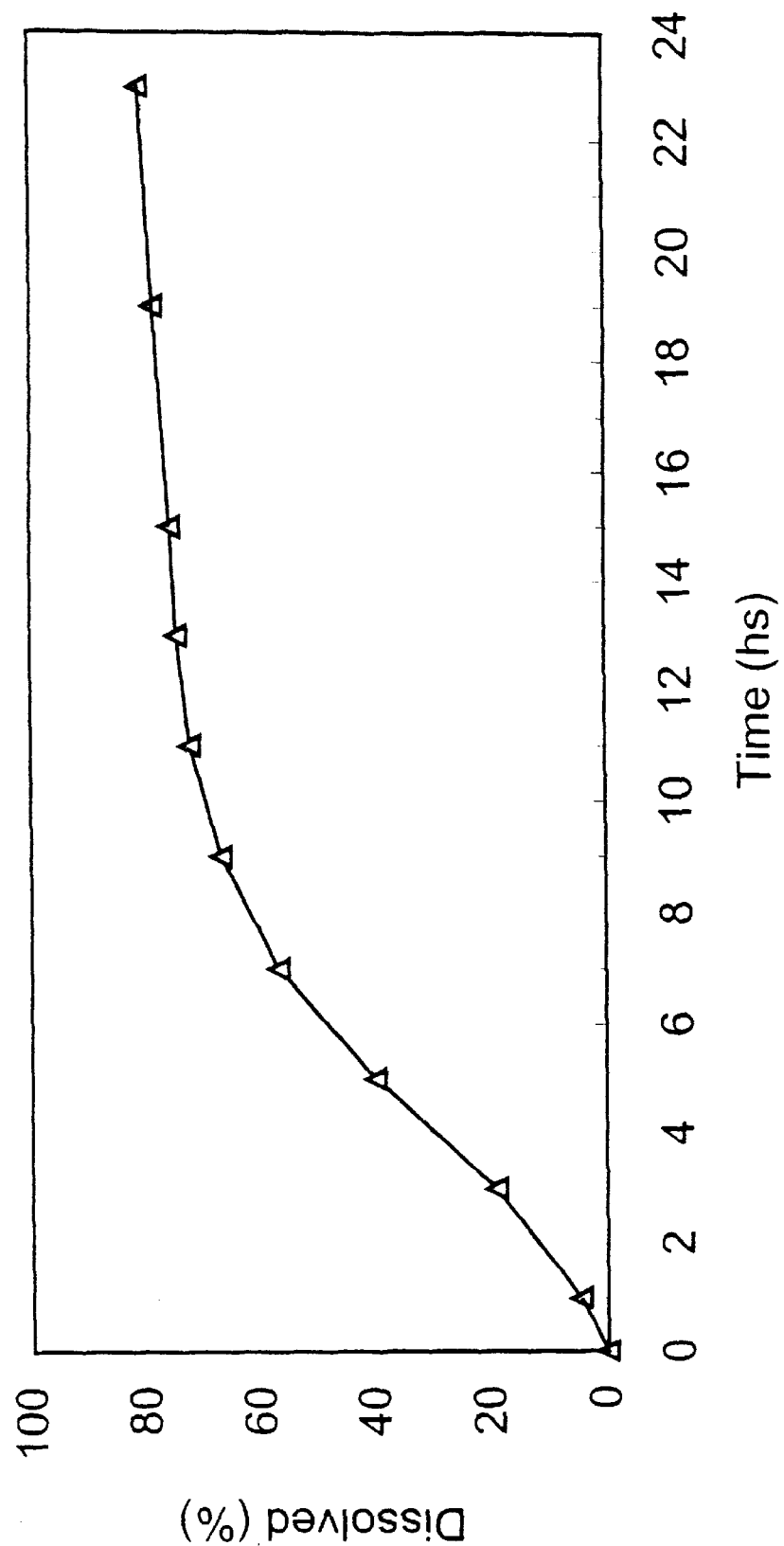

FIG. 4 depicts the release profile obtained with the device of this example. The release profile was determined in a USP Type 2 Apparatus, in distilled water, 800 ml, 100 rpm at 37°

C. The actual release data obtained are summarized below.

| Hours | Accumulated Amount Dissolved (%) |
|---|---|
| 1 | 4.7 |
| 3 | 19.1 |
| 6 | 48.5 |
| 9 | 66.9 |
| 12 | 73.3 |
| 15 | 75.5 |
| 21 | 78.5 |
| 24 | 80.9 |

EXAMPLE 4

Device Having a Rapid Release External Coating Containing Drug

A drug dosage form adapted, designed and shaped as an osmotic delivery system, containing two layers surrounding a central core, including active agent and hydrophilic polymer in the first layer and, cellulose acetate and ammonium methacrylate copolymer in the second layer, and having a rapid release external coating was manufactured as follows.

Round, biconvex-shaped cores of 7.0 mm in diameter were prepared without active agent as follows: 20.85 g of lactose monohydrate as filling material; 18.25 g of hydroxypropyl methylcellulose (HPMC of 2208 type) as hydrophilic polymer; 1.8 g of polyethylene oxide having a 4,000,000 molecular weight; 2.15 g of poly(vinylpyrrolidone); 0.30 g of red ferric oxide as coloring agent and 0.45 g of silicon dioxide were mixed and the mix was passed through a 40-mesh screen. Then, alcohol 96° was slowly added to the dry blend until a wet blend was achieved. The wet blend was passed through a 10-mesh screen and the granular mass was dried for several hours at 45° C. in a convection oven. Then the dry granulate was passed through a 20-mesh screen. The screened granulation was mixed with 0.75 g of magnesium stearate and 0.45 g of silicon dioxide (both previously passed through a 60-mesh screen) and placed into a V-blender for 5 minutes. The homogeneous mixture was subsequently compressed to form biconvex cores which individually weighed 90.0 mg.

The first layer was prepared containing the active agent as follows: 20.75 g of Cisapride monohydrate; 28.15 g of microcrystalline cellulose; 37.50 g of sodium chloride; 45.00 g of polyethylene oxide having a 200,000 molecular weight; 0.37 g of colloidal silicon dioxide and 15.75 g of poly vinylpyrrolidone were mixed and the mix was passed through a 40-mesh screen. This mixture was granulated with alcohol 96° together with 0.85 g of polysorbate 20 previously dissolved in it and all the ingredients were mixed for a few additional minutes. The granular mass was dried for several hours at 45° C. in a convection oven. Then the dry granulate was passed through a 20-mesh screen.

The screened blend was mixed with 1.25 g of magnesium stearate and 0.38 g of colloidal silicon dioxide (both previously passed through a 60-mesh screen) and placed into a V-blender for 5 minutes. The homogeneous mixture was subsequently compressed surrounding the central core which was obtained in the first part, obtaining 9.25-mm diameter biconvex tablets. The average weight of the cores was 390.0 mg.

The second layer was formed by the above tablets which were then coated with a semipermeable wall. A polymer suspension was prepared dissolving 76 weight percent of cellulose acetate; 19 weight percent of ammonium methacrylate copolymer (Eudragit RS 100, Röhn Pharma) and, 5 weight percent polyethylene glycol 400, with the total weight percent equal to 100, in a mixture of methylene chloride-methyl alcohol 80:20 v/v (volume/volume). This polymer mixture was sprayed onto the tablets in a conventional pan coater to obtain film-coated tablets whose membrane coating weighed 31.63 mg. A 0.75-mm hole was drilled through the coating in both faces of the device.

A rapid release external coating was prepared by mixing 33.48 g of ranitidine HCl, 131.02 g of microcrystalline cellulose, 25.00 g of povidone, 8.00 g of polyethylene glycol 6000, 1.70 g of polyethylene glycol 400 and 1.00 g of colloidal silicon dioxide. The mixture was blended to homogenize; then, 2.00 g of magnesium stearate was added as lubricant. This blend was tabletted to 800 mg–1000 mg/core and hardness of 8–12 kP with flat faced, 13.0-mm diameter punches. The slugs were milled by passing through a standard USP 20-mesh screen and were blended with 122.30 g of microcrystalline cellulose, 0.50 g of colloidal silicon dioxide, 5.00 g of croscarmellose sodium and 2.00 g of magnesium stearate. This final blend was compressed over the film-coated tablets by compression using biconcaves, 13.0-mm diameter punches. Coating weight: 332 mg. Hardness from 10 to 15 kp.

The final coating was prepared by mixing 10,89 g of hydroxypropyl methylcellulose 2910, 3.10 g of polyethylene glycol 6000, 3.99 g of titanium dioxide, 22.00 mg of Aluminum Lake Red Ponceau in a mixture of 280 ml of methylene chloride and 120 ml of alcohol 96°. This polymer mixture was sprayed onto the tablets in a conventional pan coater to obtain film-coated tablets whose membrane coating weighed 18 mg approximately.

EXAMPLE 5

Device Having a Controlled, Slow or Delayed Release External Coating Containing Drug A drug dosage form adapted, designed and shaped as an osmotic delivery system, containing two layers surrounding a central core, including active agent and hydrophilic polymer in the first layer and, cellulose acetate and ammonium methacrylate copolymer in the second layer, and having a delayed release external coating was manufactured as follows:

Round, biconvex-shaped cores of 7.0 mm in diameter were prepared without active agent as follows: 20.85 g of lactose monohydrate as filling material; 18.25 g of hydroxypropyl methylcellulose (HPMC of 2208 type) as hydrophilic polymer; 1.8 g of polyethylene oxide having a 4,000,000 molecular weight; 2.15 g of poly(vinylpyrrolidone); 0.30 g of red ferric oxide as coloring agent and 0.45 g of silicon dioxide were mixed and the mix was passed through a 40-mesh screen. Then, alcohol 96° was slowly added to the dry blend until a wet blend was achieved. The wet blend was passed through a 10-mesh screen and the granular mass was dried for several hours at 45° C. in a convection oven. Then the dry granulate was passed through a 20-mesh screen. The screened granulation was mixed with 0.75 g of magnesium stearate and 0.45 g of silicon dioxide (both previously passed through a 60-mesh screen) and placed into a V-blender for 5 minutes. The homogeneous mixture was subsequently compressed to form biconvex cores that individually weighed 90.0 mg.

The first layer was prepared containing the active agent as follows: 20.75 g of cisapride monohydrate; 28.15 g of microcrystalline cellulose; 37.50 g of sodium chloride; 45.00 g of polyethylene oxide having a 200,000 molecular weight; 0.37 g of colloidal silicon dioxide and 15.75 g of poly(vinylpyrrolidone) were mixed and the mixture was passed through a 40-mesh screen. This mixture was granulated with alcohol 96° together with 0.85 g of polysorbate 20 previously dissolved in it and all the ingredients were mixed for a few additional minutes. The granular mass was dried for several hours at 45° C. in a convection oven. Then the dry granulate was passed through a 20-mesh screen. The screened blend was mixed with 1.25 g of magnesium stearate and 0.38 g of colloidal silicon dioxide (both previously passed through a 60-mesh screen) and placed into a V-blender for 5 minutes. The homogeneous mixture was subsequently compressed about the central core which were obtained in the first part, to form 9.25-mm diameter biconvex tablets. The average weight of the cores was 390.0 mg.

The second layer was formed by the above tablets which were then coated with a semipermeable wall. A polymer suspension was prepared dissolving 76 weight percent of cellulose acetate; 19 weight percent of ammonium methacrylate copolymer (Eudragit RS 100, Röhn Pharma) and, 5 weight percent polyethylene glycol 400, with the total weight percent equal to 100, in a mixture of methylene chloride-methyl alcohol 80:20 v/v (volume/volume). This polymer mixture was sprayed onto the tablets in a conventional pan coater to obtain film-coated tablets whose membrane coating weighed 31.63 mg. A 0.75-mm hole was drilled through the coating in both faces of the device.

A delayed release external coating was prepared by mixing 33.48 g of ranitidine HCl, 131.02 g of microcrystalline cellulose, 25.00 g of povidone, 8.00 g of polyethylene glycol 6000, 1.70 g of polyethylene glycol 400 and 1.00 g of colloidal silicon dioxide. The mixture was blended to homogenize; then, 2.00 g of magnesium stearate was added as lubricant. This blend was tabletted to form 800 mg–1000 mg cores having a hardness of 8–12 kP with flat faced, 13.0-mm diameter punches. The slugs were milled by passing through a standard USP 20-mesh screen and were blended with 122.30 g of microcrystalline cellulose, 0.50 g of colloidal silicon dioxide, 5.00 g of croscarmellose sodium and 2.00 g of magnesium stearate. This final blend was compressed over the film-coated tablets by compression using biconcaves, 13.0-mm diameter punches. Coating weight: 332 mg. Hardness from 10 to 15 kp.

The final coating was prepared by mixing 21.80 g of methacrylic acid copolymer, USP Type A, 1.45 g of polyethylene glycol 6000, 4.60 g of titanium dioxide, 7.00 g of talc and 0.15 mg of Red Ferric Oxide in 780 ml of isopropyl alcohol. This polymer mixture was sprayed onto the tablets in a conventional pan coater to obtain film-coated tablets which membrane coating weighed 35 mg approximately.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

I claim:

1. A device for the controlled delivery of at least one active agent to an environment of use, wherein the device comprises:

a core expandable in a fluid from the environment of use, the core being approximately centrally located in the device;

a layer comprising at least one first active agent, wherein the layer is in contact with and surrounds the core; and a membrane in contact with and surrounding the layer and comprising at least one preformed passageway for delivery of the at least one active agent by osmotic pumping and plural micropores for delivery of the at least one active agent by diffusion, and the membrane further comprising one or more cellulose esters, one or more poly(methacrylate) copolymer salts and one or more plasticizers, wherein the membrane permits delivery of the at least one active substance through a combination of diffusion and osmotic pumping.

2. A device according to claim 1 further comprising a drug-containing coat external to the membrane and comprising a second active agent, wherein the drug-containing coat provides an immediate, rapid, controlled or delayed release of the second active agent and the external coat surrounds at least a portion of the membrane.

3. A device according to claim 2, wherein the first and second active agents are different and are independently selected at each occurrence from the group consisting of an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, antidepressant agent, antidiabetic agent, antineoplastic agent, anti-psychotic agent, neuroleptic agent, antihypertensive agent, hypnotic agent, sedative agent, anxiolytic energizer agent, antiparkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, anti-ulcerant agent, anti-flatulent agent, anti-incontinence agent, and cardiovascular agent.

4. A device according to claim 3, wherein the first active agent is a prokinetic agent and the second active agent is a gastric acid secretion inhibitor agent.

5. A device according to claim 3, wherein the first active agent is a decongestant and the second active agent is an antihistamine.

6. A device according to claim 3, wherein the first active agent is a first anti-incontinence agent and the second active agent is a different second anti-incontinence agent.

7. A device according to claim 6, wherein the anti-incontinence agents are selected from the group consisting of oxybutynin, tolterodine and darifenacin.

8. A device according to claim 3, wherein the first active agent is a first antihypertensive agent and the second active agent is a different second antihypertensive agent.

9. A device according to claim 8, wherein the antihypertensive agents are selected from the group consisting of a calcium channel blocker agent, an angiotensin converting enzyme inhibitor agent, a diuretic agent and a beta-adrenergic antagonist agent.

10. A device according to claim 3, wherein the first active agent is an antidepressant agent and the second active agent is an anti-psychotic agent.

11. A device according to claim 3, wherein the first active agent is a first analgesic or anti-inflammatory agent, and the second active agent is a different second analgesic or anti-inflammatory agent.

12. A device according to claim 11, wherein the analgesic and anti-inflammatory agents are selected from the group consisting of an non-steroidal anti-inflammatory agent, a steroidal anti-inflammatory agent, an opioid receptor agonist agent, and a selective or specific COX-II inhibitor agent.

13. A device according to claim 3, wherein the first active agent is an antiviral agent and the second active agent is an antihistamine agent.

14. A device according to claim 3, wherein the first active agent is a muscle relaxant agent and the second active agent is an anti-inflammatory or analgesic agent.

15. A device according to claim 14, wherein the first active agent is pridinol and the second active agent is a selective or specific COX-II inhibitor agent.

16. A device according to claim 2, wherein the first and second active agents are the same and are selected from the group consisting of an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, antidepressant agent, antidiabetic agent, antineoplastic agent, anti-psychotic agent, neuroleptic agent, antihypertensive agent, hypnotic agent, sedative agent, anxiolytic energizer agent, antiparkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, anti-ulcerant agent, anti-flatulent agent, anti-incontinence agent, and cardiovascular agent.

17. A device according to claim 1, wherein the membrane comprises about 1 to 99 weight percent of one or more cellulose esters, about 84 to 0.5 weight percent of one or more poly(methacrylate) copolymer salts and about 15 to 0.5 weight percent of one or more plasticizers.

18. A device according to claim 1, wherein the cellulose ester is selected form the group consisting of cellulose acylate, cellulose diacylate, cellulose triacylate, cellulose acetate, cellulose diacetate, cellulose triacetate and combinations thereof.

19. A device according to claim 1, wherein the poly(methacrylate) copolymer salt is poly(ammonium methacrylate) copolymer.

20. A device according to claim 1, wherein the plasticizer is selected from the group consisting of acetyl triethyl citrate, acetyl tributyl citrate, triethyl citrate, acetylated monoglycerides, glycerol, poly(ethylene glycol), triacetin, propylene glycol, dibutyl phthalate, diethyl phthalate, dipropyl phthalate, dimethyl phthalate, dioctyl phthalate, dibutyl sebacate, dimethyl sebacate, castor oil, glycerol monostearate, and coconut oil.

21. A device according to claim 1, wherein the first active agent is one of a biologically active agent, pharmacologically active agent, medicine, nutrient, food product, vitamin, insecticide, pesticide, herbicide, microbicide, algaecide, fungicide, grow regulating substance, parasiticide, sterilant, fertility promoter, biocide, rodenticide, disinfectant, plant growth promoter, preservative, fertility inhibitor, deodorant, catalysts, food supplement and cosmetic.

22. The device of claim 1, wherein the layer further comprises at least one of an osmagent and an osmopolymer; the expandable core further comprises at least one expandable hydrophilic polymer and, optionally, an osmagent.

23. The device of claim 22, wherein the membrane comprises about 1 to 99 weight percent of one or more cellulose esters, about 84 to 0.5 weight percent of one or more poly(methacrylate) copolymer salts and about 15 to 0.5 weight percent of one or more plasticizers.

24. The device of claim 23, wherein the expandable hydrophilic polymer is one or more of hydroxypropyl methylcellulose, alkylcellulose, hydroxyalkylcellulose, poly (alkylene oxide), and combinations thereof; and the at least one cellulose ester is independently selected from the group consisting of cellulose acylate, cellulose diacylate, cellulose triacylate, cellulose acetate, cellulose diacetate, cellulose triacetate and combinations thereof.

25. The device of claim 23, wherein the at least one poly(methacrylate) copolymer salt is a poly(ammonium methacrylate) copolymer.

26. The device of claim 2, wherein the layer further comprises at least one of an osmagent and an osmopolymer; the expandable core further comprises at least one expandable hydrophilic polymer and, optionally, an osmagent.

27. The device of claim 26, wherein the membrane comprises about 1 to 99 weight percent of one or more cellulose esters, about 84 to 0.5 weight percent of one or more poly(methacrylate) copolymer salts and about 15 to 0.5 weight percent of one or more plasticizers.

28. The device of claim 27, wherein the expandable hydrophilic polymer is one or more of hydroxypropyl methylcellulose, alkylcellulose, hydroxyalkylcellulose, poly (alkylene oxide), and combinations thereof; and the at least one cellulose ester is independently selected from the group consisting of cellulose acylate, cellulose diacylate, cellulose triacylate, cellulose acetate, cellulose diacetate, cellulose triacetate and combinations thereof.

29. The device of claim 27, wherein the at least one poly(methacrylate) copolymer salt is a poly(ammonium methacrylate) copolymer.

30. A device for the controlled delivery of at least one active agent to an environment of use, wherein the device comprises:

a core expandable in a fluid from the environment of use, the core being approximately centrally located in the device;

a layer comprising at least one first active agent, wherein the layer is in contact with and surrounds the core; and a membrane in contact with and surrounding the layer and comprising one or more cellulose esters, one or more poly(methacrylate) copolymer salts and one or more plasticizers, wherein the membrane permits delivery of the at least one active substance through a combination of diffusion and osmotic pumping.

* * * * *